United States Patent
Gerber et al.

(10) Patent No.: US 12,016,740 B2
(45) Date of Patent: Jun. 25, 2024

(54) DOCKING SYSTEM TO STABILIZE EYEBALL DURING INTRAOCULAR SURGERY

(71) Applicant: THE REGENTS OF THE UNIVERSITY OF CALIFORNIA, Oakland, CA (US)

(72) Inventors: Matthew Gerber, Los Angeles, CA (US); Yu-Hsiu Lee, Los Angeles, CA (US); Tsu-Chin Tsao, Los Angeles, CA (US); Jacob Rosen, Los Angeles, CA (US); Jean-Pierre Hubschman, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 918 days.

(21) Appl. No.: 17/021,925

(22) Filed: Sep. 15, 2020

(65) Prior Publication Data
US 2021/0000566 A1 Jan. 7, 2021

Related U.S. Application Data

(63) Continuation-in-part of application No. PCT/US2019/022986, filed on Mar. 19, 2019.
(60) Provisional application No. 62/645,517, filed on Mar. 20, 2018.

(51) Int. Cl.
*A61B 90/50* (2016.01)
*A61B 90/20* (2016.01)
*A61F 9/007* (2006.01)
*A61B 90/00* (2016.01)

(52) U.S. Cl.
CPC .............. *A61B 90/50* (2016.02); *A61B 90/20* (2016.02); *A61F 9/00736* (2013.01); *A61B 2090/3735* (2016.02); *A61B 2217/005* (2013.01); *A61B 2217/007* (2013.01); *A61B 2562/0247* (2013.01)

(58) Field of Classification Search
CPC . A61B 90/50; A61B 90/20; A61B 2090/3735; A61B 2217/005; A61B 2217/007; A61B 2562/0247; A61F 9/00736
USPC ........................................................ 351/245
See application file for complete search history.

(56) References Cited

U.S. PATENT DOCUMENTS

| 4,429,696 | A | 2/1984 | Hanna |
| 5,626,594 | A | 5/1997 | Smith |
| 5,989,272 | A | 11/1999 | Barron et al. |
| 6,899,707 | B2 | 5/2005 | Scholler et al. |

(Continued)

OTHER PUBLICATIONS

International Search Report and Written Opinion, issued in Int'l. Appln. No. PCT/US2019/022986, 13 pages (dated May 31, 2019).

(Continued)

*Primary Examiner* — Joseph P Martinez
*Assistant Examiner* — Grant A Gagnon
(74) *Attorney, Agent, or Firm* — Foley & Lardner LLP

(57) ABSTRACT

A docking system for intraocular surgery that is configured to simultaneously: (1) physically stabilize a position and an orientation of an eye during intraocular surgical procedures; (2) preserve an unobstructed path for optical instruments; (3) provide access to the eye that allows for tool movement; (4) maintain eyeball hydration and improve the scan quality of an imaging system, such as an OCT system or a surgical microscope and may maintain or control an intraocular pressure of the eye to a stable, desired level during surgical procedures.

15 Claims, 9 Drawing Sheets

(56) References Cited

U.S. PATENT DOCUMENTS

| | | |
|---|---|---|
| 8,845,624 B2 | 9/2014 | Raksi et al. |
| 2007/0093795 A1 | 4/2007 | Melcher et al. |
| 2011/0022035 A1 | 1/2011 | Porter et al. |
| 2011/0152774 A1 | 6/2011 | Lopez et al. |
| 2011/0190741 A1 | 8/2011 | Deisinger et al. |
| 2011/0319873 A1 | 12/2011 | Raksi et al. |
| 2012/0099077 A1 | 4/2012 | Abt |
| 2014/0128821 A1 | 5/2014 | Gooding et al. |

OTHER PUBLICATIONS

Supplementary Search Report on European Application No. 19772473.5 dated Nov. 24, 2021.

(a) Examplary Embodiment with Tool Access:

(b) Existing Design without Tool Access:

DOCKING SYSTEM TO STABILIZE EYEBALL DURING INTRAOCULAR SURGERY

CROSS-REFERENCE TO RELATED APPLICATIONS

This application is a continuation-in-part of International Application No. PCT/US2019/022986, filed Mar. 19, 2019, which claims the benefit of U.S. Provisional Application No. 62/645,517, filed Mar. 20, 2018, the contents of which are incorporated herein by reference in their entirety.

STATEMENT REGARDING FEDERALLY SPONSORED RESEARCH OR DEVELOPMENT

This invention was made with government support under EY024065, awarded by the National Institutes of Health. The government has certain rights in the invention.

TECHNICAL FIELD

This disclosure generally relates to a physical interface between a light-based device and an eyeball during intraocular surgery.

BACKGROUND

Intraocular medical conditions are treated with delicate microsurgical procedures that rely on visualization of delicate tissues within a small and constrained space of an eye. Optical coherence tomography (OCT) can be used to improve intraocular visualization by imaging small membranes and anatomical features to reveal features that would otherwise remain invisible or difficult to perceive by a surgeon, thereby improving surgical outcomes. In addition, OCT is capable of providing fast, small-scale, and accurate measurements which allow for the possibility of real-time guidance to the surgeon or to an autonomous robotic surgical system. In addition to OCT, a surgical microscope can be used to visualize features inside the eye. In addition to imaging devices, laser-based manipulation devices such as femtosecond laser systems can be used to cut, slice, or physically change the eye.

Despite the advantages of OCT systems, surgical microscopes, and laser-based surgical devices, the quality of both imaging and light-based manipulation systems can suffer from the nature of a surgical environment. First, the constant motion either from the patient movement or when surgical tools are manipulated inside the eyeball can result in high levels of noise, data distortion, and physically inaccuracy within the visualized area. Second, OCT scan quality in particular can be dependent on the presence of a fluid medium between an imaging probe and anatomy to be scanned; therefore, presence of a fluid medium can maintain eye hydration in addition to improving visualization quality. Further, the imaging system is located in a patient sterile field but cannot itself be adequately sterilized, thereby constraining its use and integration into other systems, such as robotic surgical systems. In addition, while docking systems may exist, none are capable of simultaneously allowing for a surgical instrument to manipulate the eye when the docking is engaged. Allowing simultaneous docking and instrument manipulation would provide some or all of the abovementioned benefits without comprising the need to perform surgical manipulation.

It is against this background that a need arose to develop the embodiments described herein.

SUMMARY

Embodiments of this disclosure are directed to a physical interface between a probe of an imaging system, such as a surgical microscope or an OCT system, and an eyeball during intraocular surgery. In particular, in some embodiments, a docking system and an associated method are provided to secure or stabilize the eyeball relative to the imaging probe, to preserve an unobstructed path for optical instruments, such as laser-assisted surgical systems or OCT, to allow for the use of intraocular surgical instruments or tools within the eyeball, to maintain the eyeball hydration, and to facilitate real-time image acquisition during intraocular surgery.

In some embodiments, a docking system is provided to secure an eyeball during intraocular surgery and constrain it relative to an imaging probe. The docking system includes a rigid support structure that is configured to accommodate and receive the imaging probe at one end of the support structure and to accommodate and receive the eyeball at another end of the support structure. A separation layer is provided within the support structure to compartmentalize or separate an interior of the support structure into a patient sterile field and a non-sterile imaging probe field. A retaining mechanism is provided at the end of the support structure that receives the eyeball, such as a suction attachment, to secure the eyeball relative to the support structure. One or more flexible ports are provided extending through a sidewall of the support structure to allow surgical instruments or tools to be inserted through the flexible ports.

Embodiments of the docking system can be used to simultaneously (1) physically stabilize a position and an orientation of an eye during intraocular surgical procedures, (2) preserve an unobstructed path for optical instruments, (3) provide access to the eye that allows for tool movement, (4) maintain eyeball hydration and improve the scan quality of an imaging system, such as an OCT system or a surgical microscope, and may maintain or control an intraocular pressure of the eye to a stable, desired level during surgical procedures.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Figure 1:
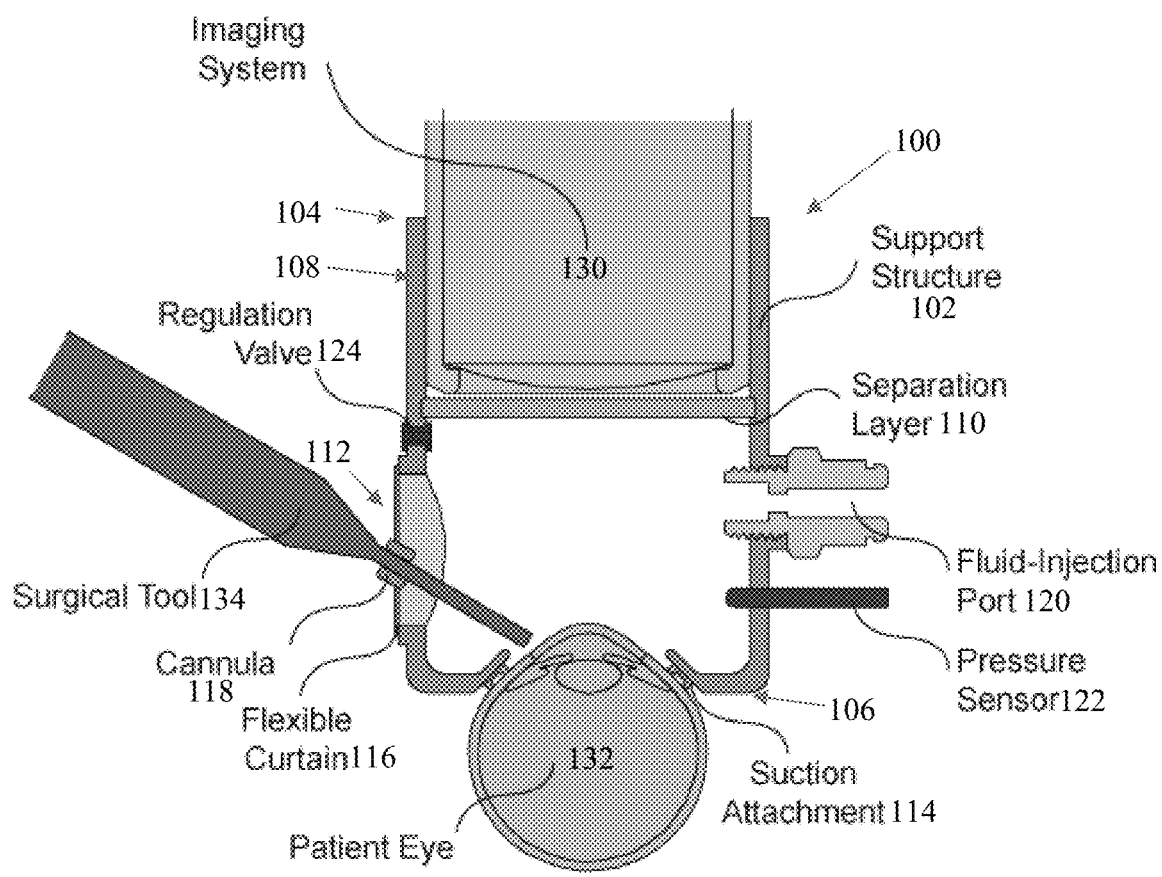
FIG. 1 shows a docking system according to some embodiments.

Referring to FIG. 1, an imaging probe 130 is located at a distance from an eyeball 132. According to some embodiments, a docking system 100 is provided that includes a rigid support structure 102 having a first end 104 that accommodates, receives, and fits over the imaging probe 130, and having a second end 106 that accommodates and receives the eyeball 132 to secure the eyeball 132 in place relative to the imaging probe 130. The support structure 102 is hollow and includes a sidewall 108 that forms a generally cylindrical shape. A separation layer 110 is disposed within an interior of the support structure 102 between the imaging probe 130 and the eyeball 132 to separate a patient sterile field from a non-sterile field of the imaging probe 130, without interfering with imaging capabilities of the imaging probe 130. For example, the separation layer 110 can be formed of, or can include, a light transmissive material (e.g., at least about 80%, at least about 85%, or at least about 90% transmissive) relative to electromagnetic radiation detected by the imaging probe 130. At least one flexible tool port 112 is disposed extending through an opening in the sidewall 108 of the support structure 102, such that a surgical instrument or tool 134 can pass through the flexible port 112, extending to an RCM at or inside the eyeball 132. The flexible port 112 can accommodate tool movement during a surgical procedure as well as tool insertion and extraction. A retaining mechanism 114 is disposed at or adjacent to the second end 106 of the support structure 102, such a passive suction attachment, for securing the eyeball 132 relative to the support structure 102. As shown in FIG. 1, the suction attachment is generally circular in geometry, such as in the form of a ring, and can cover an entire anterior segment of the eyeball 132 (cornea/limbus/sclera).

Figure 2:
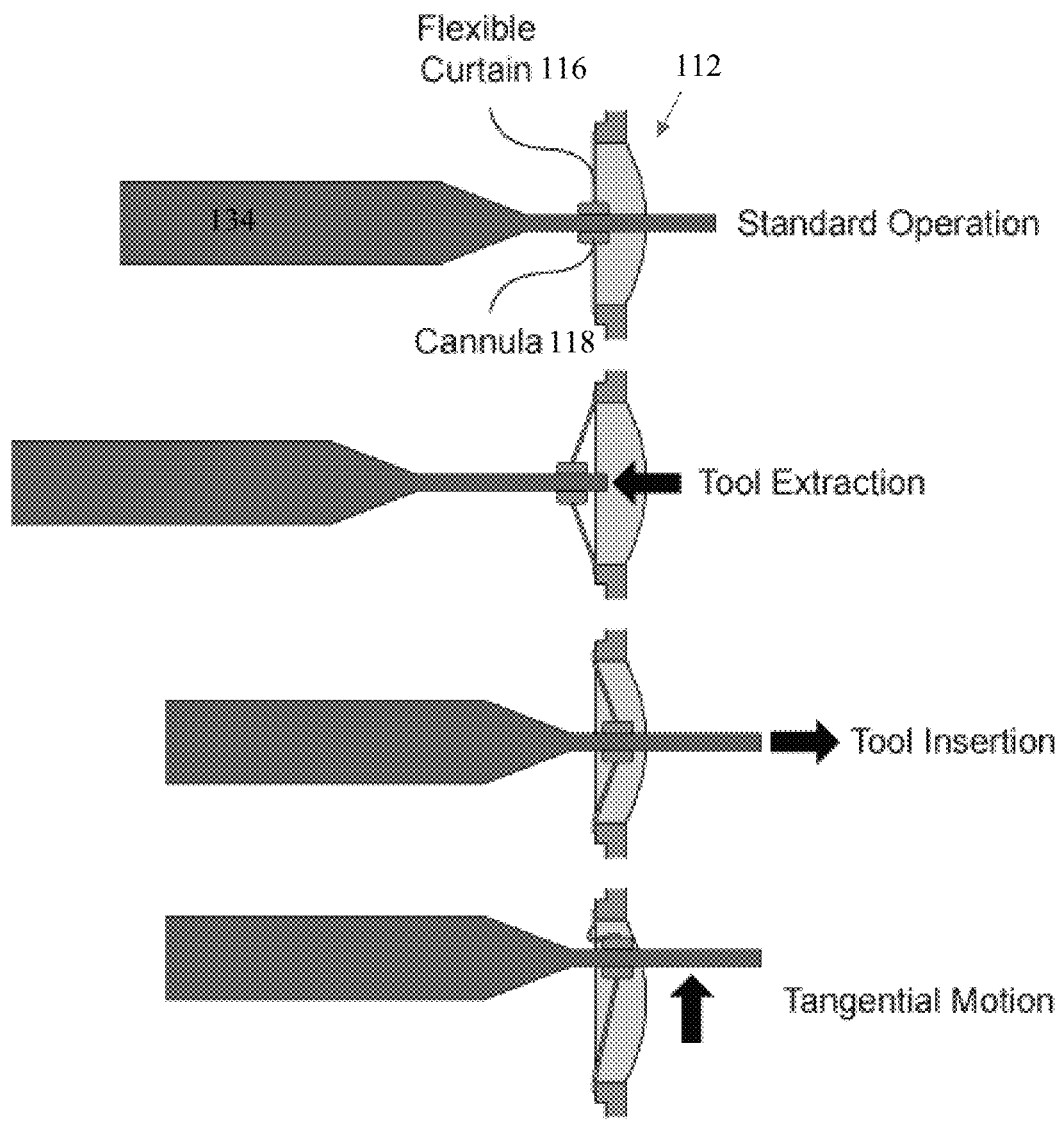
FIG. 2 shows a flexible port of the docking system of FIG. 1, according to some embodiments.

Referring to FIG. 2, the flexible port 112 of the docking system 100 is shown. The flexible port 112 includes two main components: (1) a flexible curtain 116, such as formed of an elastomer, that maintains a fluid seal between the interior and an exterior of the support structure 102 and (2) a tool cannula 118 that extends through the flexible curtain 116 and forms a seal with the surgical tool 134. The flexible curtain 116 accommodates both an in/out motion and a tangential motion of the tool 134, as shown in FIG. 2. During normal operation, this flexibility allows the tool 134 to move relatively unobstructed, whereas during insertion/extraction of the tool 134, the flexible curtain 116 is pushed/pulled along with the tool 134. The tool cannula 118 can be integrated into the flexible curtain 116 to provide a substantially continuous fluid seal between the interior and exterior of the support structure 102. The tool cannula 118 forms a seal around the tool 134, allowing for relatively unobstructed tool motion (low friction) while maintaining the fluid seal.

Figure 3:
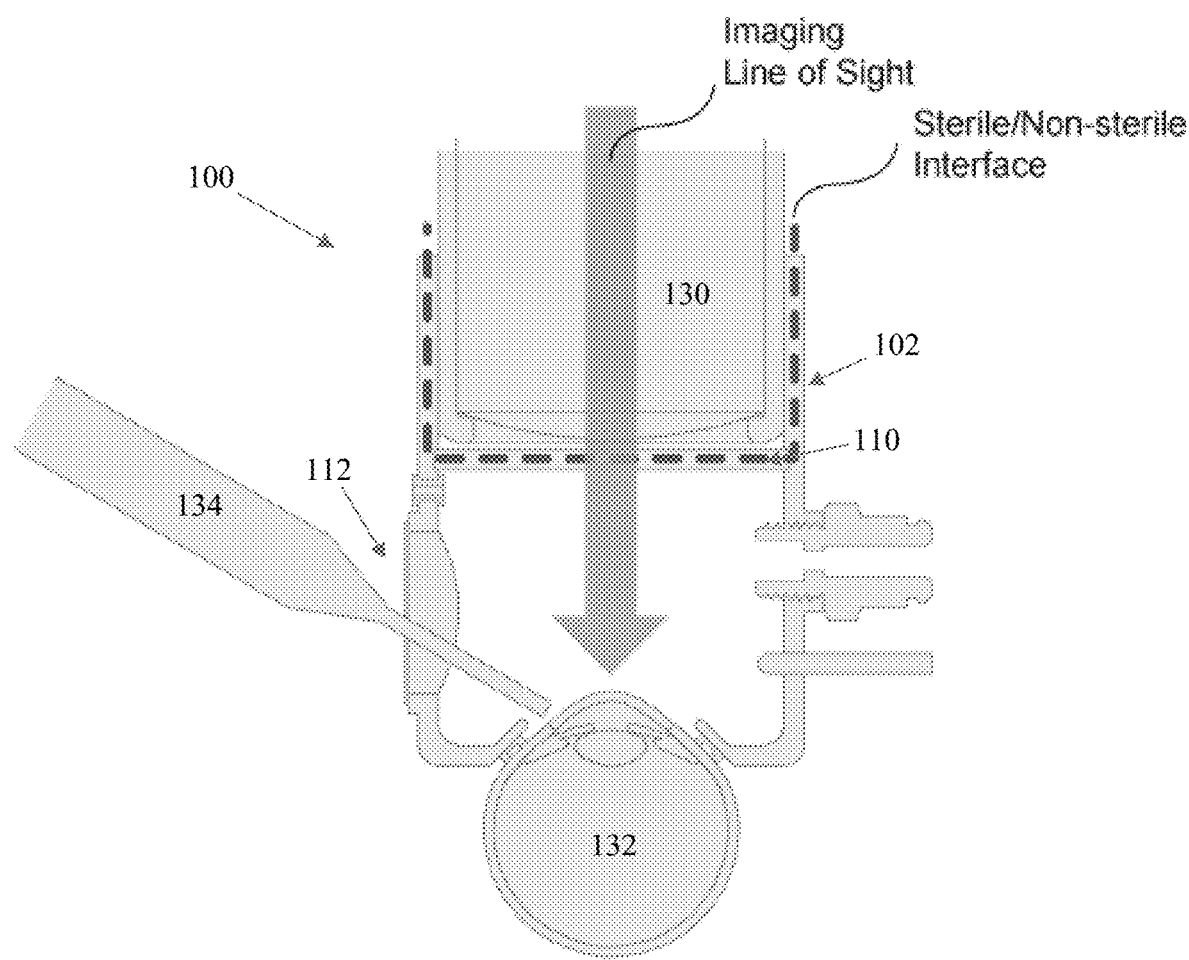
FIG. 3 shows an interface between sterile and non-sterile surgical fields of the docking system of FIG. 1, according to some embodiments.

Referring to FIG. 3, an interface between sterile and non-sterile surgical fields of the docking system 100 is shown. This interface is composed of a portion of the support structure 102 accommodating the imaging probe 130 along with the separation layer 110, configured such that the interface does not interfere with imaging capabilities. Components of the docking system 100 in the sterile field can be configured specifically to comply with surgical operating theater criteria for sterility, or can be formed of inexpensive materials and can be disposable. Regardless of how the flexible port 112 moves in response to tool movement, an imaging line of sight is maintained and remains unblocked, other than by the tool 134 itself.

Figure 4:
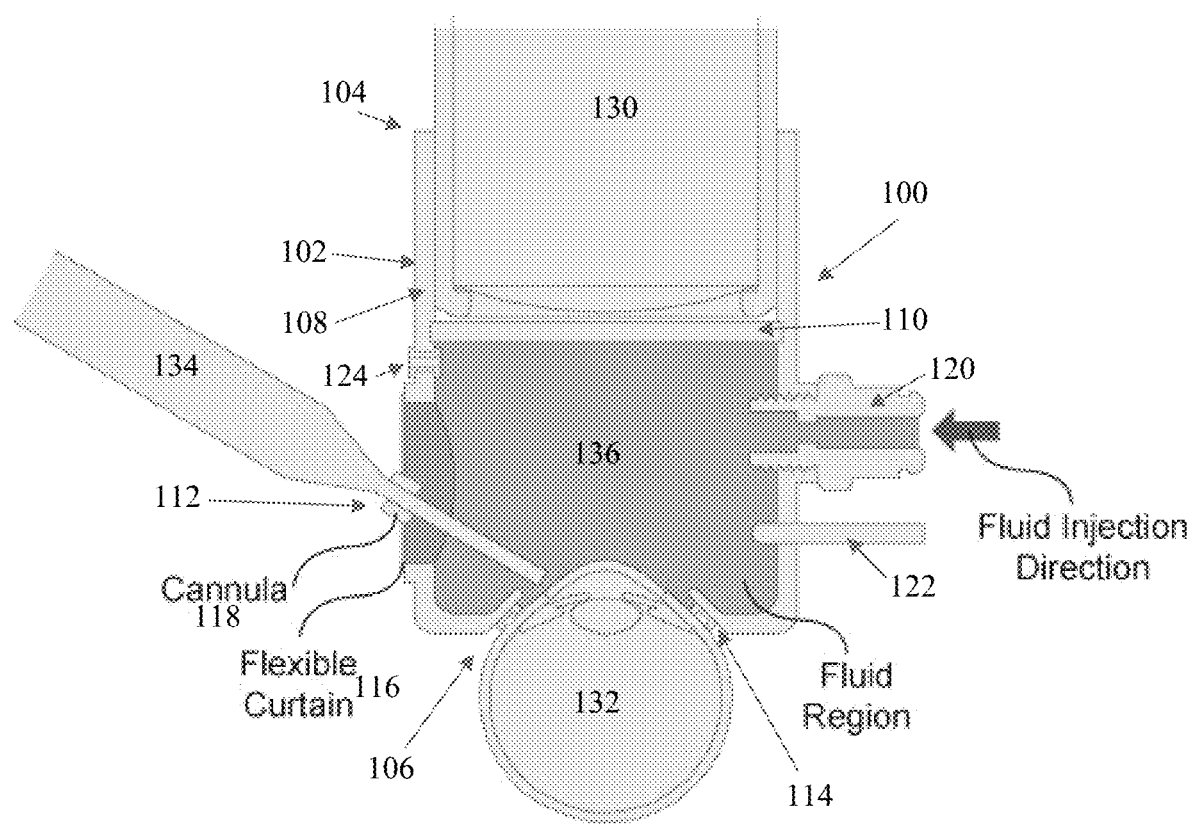
FIG. 4 shows a lubricating fluid introduced through a fluid-injection port of the docking system of FIG. 1, according to some embodiments.

Referring to FIG. 4 in combination with FIG. 1, a lubricating fluid (e.g., a lubricating liquid) 136 is introduced through a fluid-injection port 120 disposed extending through another opening in the sidewall 108 of the support structure 102, such that the fluid 136 can fill a portion of the interior (serving as a fluid region/cavity) between the separation layer 110 and the patient's eyeball 132. This fluid 136 serves the following purposes: (1) it maintains hydration or lubrication of the eyeball 132, (2) it maintains an internal pressure of the docking system 100 and can be used to balance a force of the retaining mechanism 114, and (3) it improves a quality of an imaging system by providing a fluid medium (such as for an OCT probe). It is noted that the flexible curtain 116 together with the tool cannula 118 maintain a fluid seal between the interior and exterior of the support structure 102. As shown in FIG. 1, a pressure sensor 122 and a regulation valve 124 are each disposed extending through the sidewall 108 of the support structure 102, where the pressure sensor 122 measures the internal pressure of the docking system 100, and the regulation valve 124 allows for controlled release or removal of the fluid 136 in the event the internal pressure exceeds a specified threshold.

Figure 5:
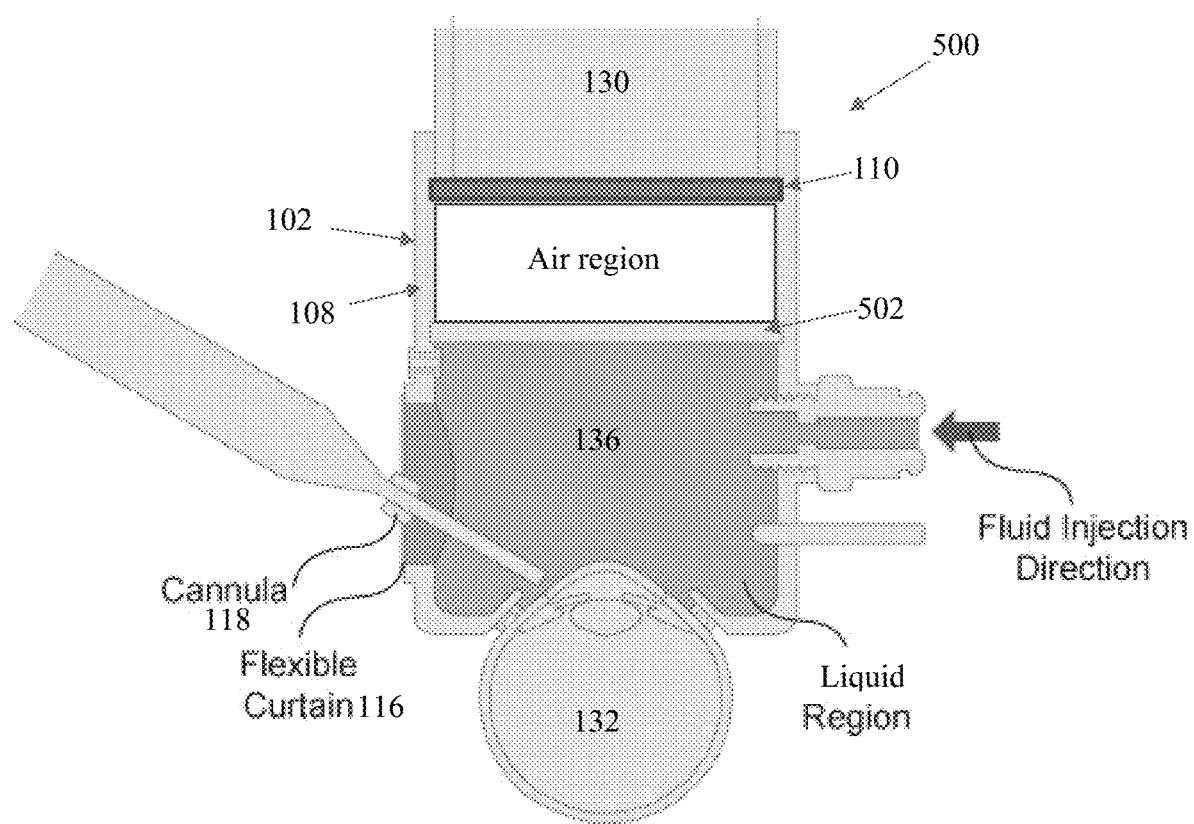
FIG. 5 shows a docking system according to additional embodiments.

FIG. 5 shows a docking system 500 according to additional embodiments. Certain features of the docking system 500 are similarly implemented as explained for the docking system 100, and repeated explanation of those features is omitted. As shown in FIG. 5, the docking system 500 further includes a barrier layer 502, which is disposed within the interior of the support structure 102 between the separation layer 110 and the eyeball 132 to separate or compartmentalize the sterile field into an air region/cavity and a liquid region/cavity. The air region/cavity can contain air (or another gas or can be evacuated), and the barrier layer 502 forms a seal with the sidewall 108 of the support structure 102 to block the lubricating fluid 136 from entering the air region/cavity. The provision of the air region/cavity can further improve a scan quality of an imaging system. The barrier layer 502 can be formed of, or can include, a light transmissive material (e.g., at least about 80%, at least about 85%, or at least about 90% transmissive) relative to the electromagnetic radiation detected by the imaging probe 130.

Figure 6:
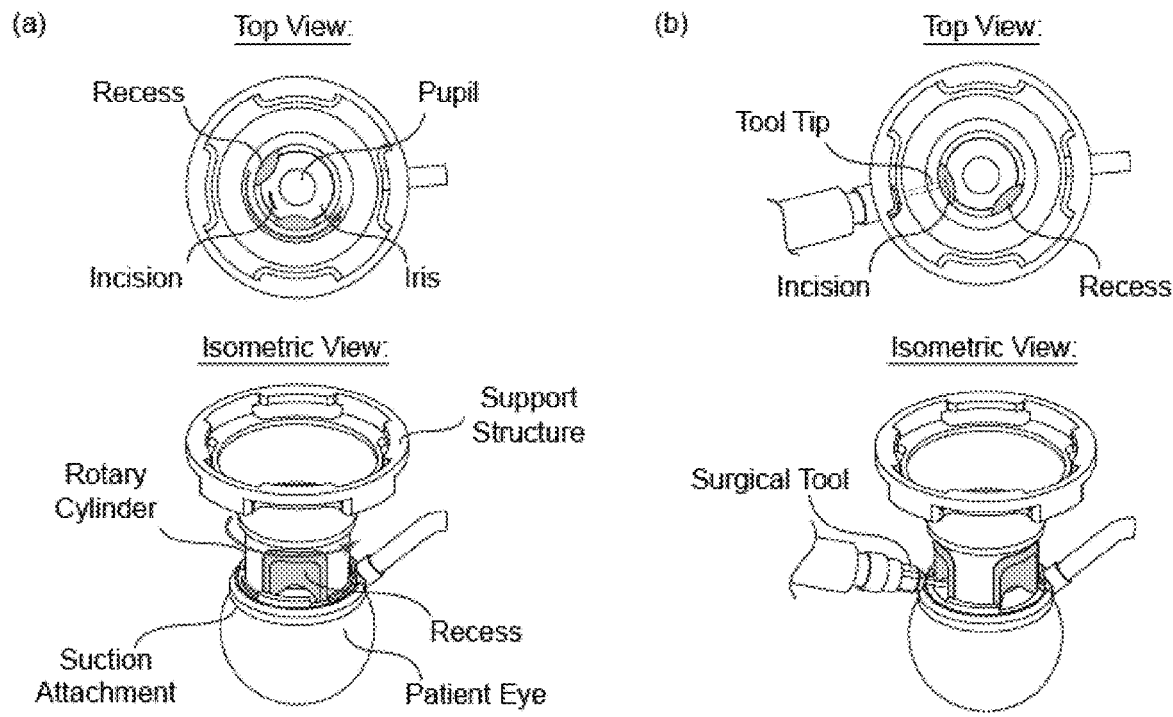
FIG. 6 shows an embodiment wherein the incision site is separated from the imaging area by recess features, and the said features are configurable to accommodate for laser-assisted procedures, such as an incision.

FIG. 6 shows an embodiment in which the incision site is separated from the center imaging area by the introduction of one or multiple recess features. To preserve unobstructed optical path for laser-assisted procedures, such as an incision, the recess features are configurable via the rotation of the rotary cylinder between the support structure and the suction attachment. The recess can accommodate for the tool access while providing sufficient stabilization of the eyeball without a flexible side wall.

Figure 7:
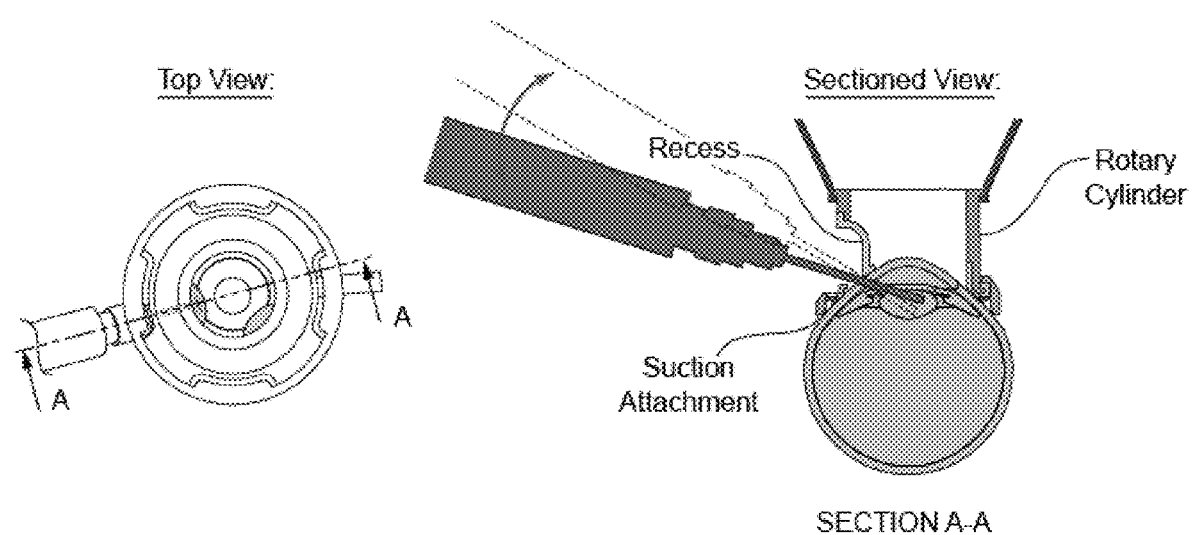
FIG. 7 shows the cross-sectional view of the docking system of FIG. 6, illustrating the realization of the separation between the incision site and the imaging area.

Referring to FIG. 7, a cross-sectional view of the embodiment in FIG. 6 is shown. The cavity above the eyeball may be filled with lubricating fluid as is in FIG. 4 to maintain the hydration and enhance imaging quality. The fluid-injection port, the pressure sensor, and the regulation valve may be added for maintaining a regulated fluid pressure above the eyeball. The recess and the suction attachment may be realized using deformable materials such as silicone rubber or elastomer to provide better sealing. The suction attachment can also serve as a leak barrier for corneal leakage, or, a trocar may be used for the same functionality.

Figure 8:
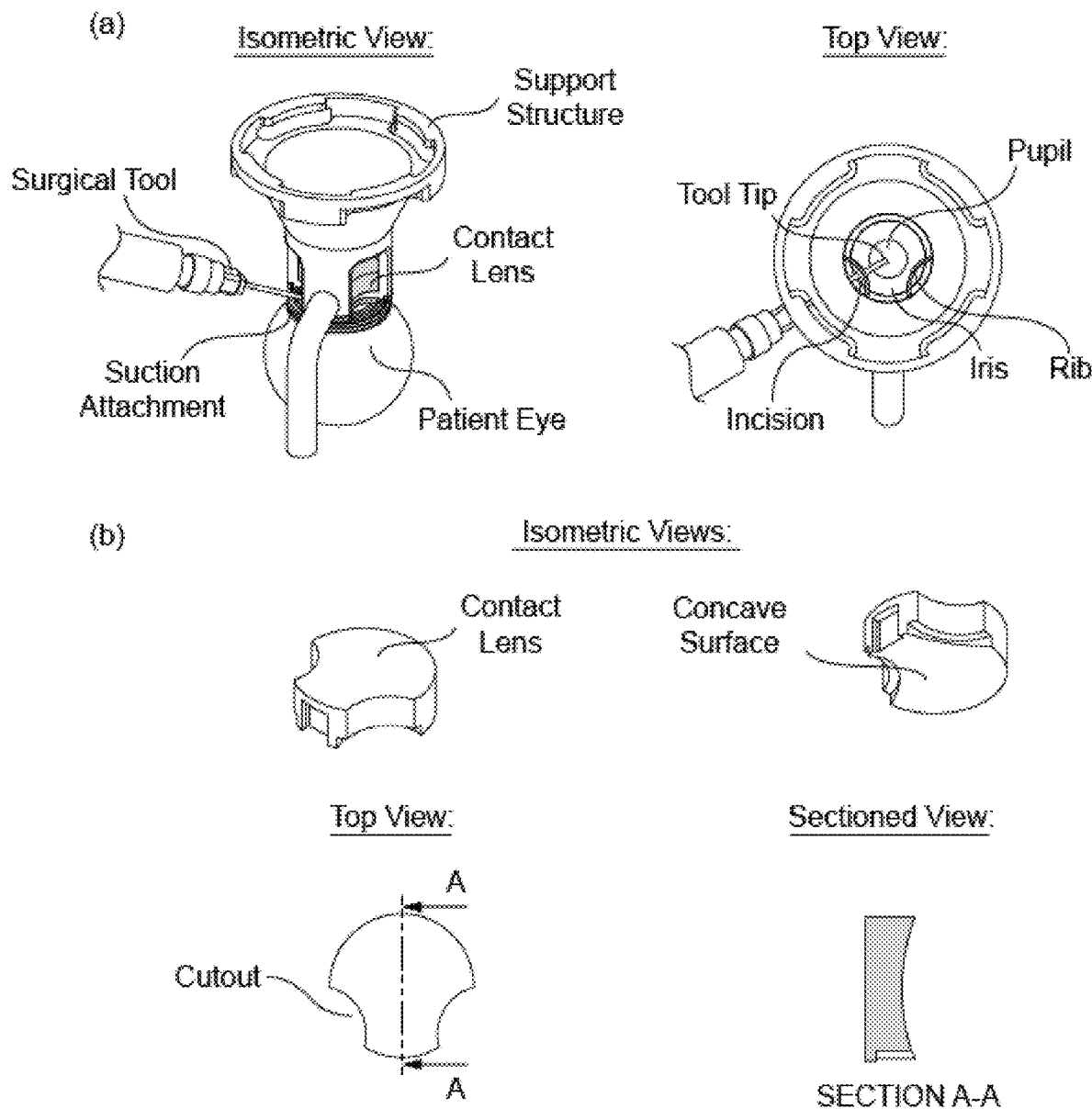
FIG. 8 shows another embodiment wherein a vacuum chamber is incorporated to increase the effective suction area via the use of a contact lens that conforms to the eye anatomy.

FIG. 8 shows another embodiment in which a contact lens is used to further increase the effective suction area and to improve the eyeball stabilization. The contact lens has one or multiple cutouts to accommodate for tool access, and may separate the incision cite with the rib features shown. The index of refraction of the contact lens is different from the region outside the rib, which is exposed to the atmosphere, and can be calibrated before the surgery. The concave surface of the contact lens is shaped to conform to the eye anatomy without introducing excessive stress.

Figure 9:
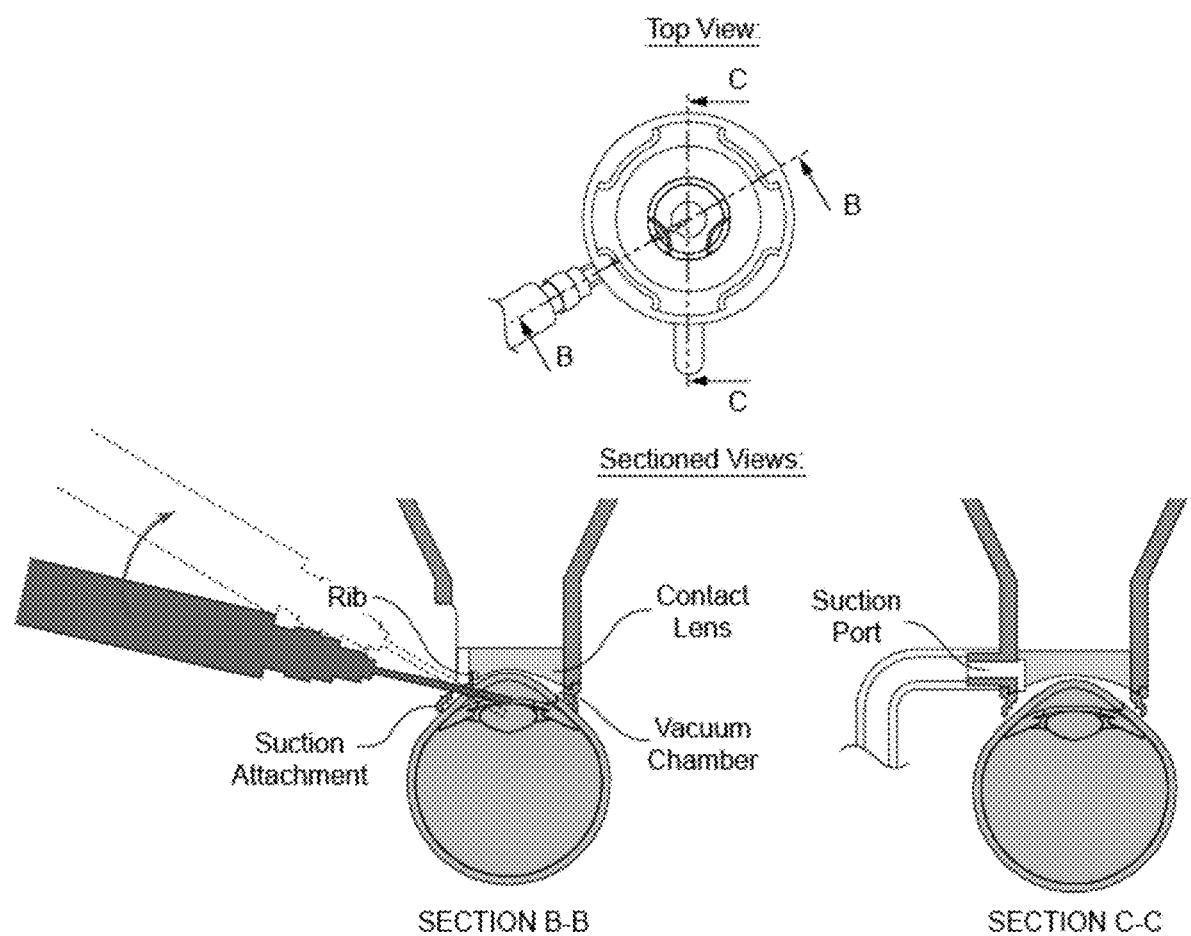
FIG. 9 shows the cross-sectional view of the docking system of FIG. 8, illustrating the realization of the said vacuum chamber.

Referring to FIG. 9, two cross-sectional views of the embodiment in FIG. 8 are shown. The suction force of the embodiment in FIG. 8 is increased by enclosing a vacuum chamber with larger area between the contact lens and the eyeball, as opposed to the ring suction design. Another soft lens may be introduced in this space to accommodate for a wider range of eye anatomy. Lubricating fluid is applied between the contact lens and eyeball to maintain the hydration and improve the imaging quality. The suction attachment, including the contact point beneath the rib feature, may be realized by deformable materials such as silicone rubber or elastomer to provide better sealing. The suction attachment can also serve as a leak barrier for corneal leakage, or, a trocar may be used for the same functionality.

Figure 10:
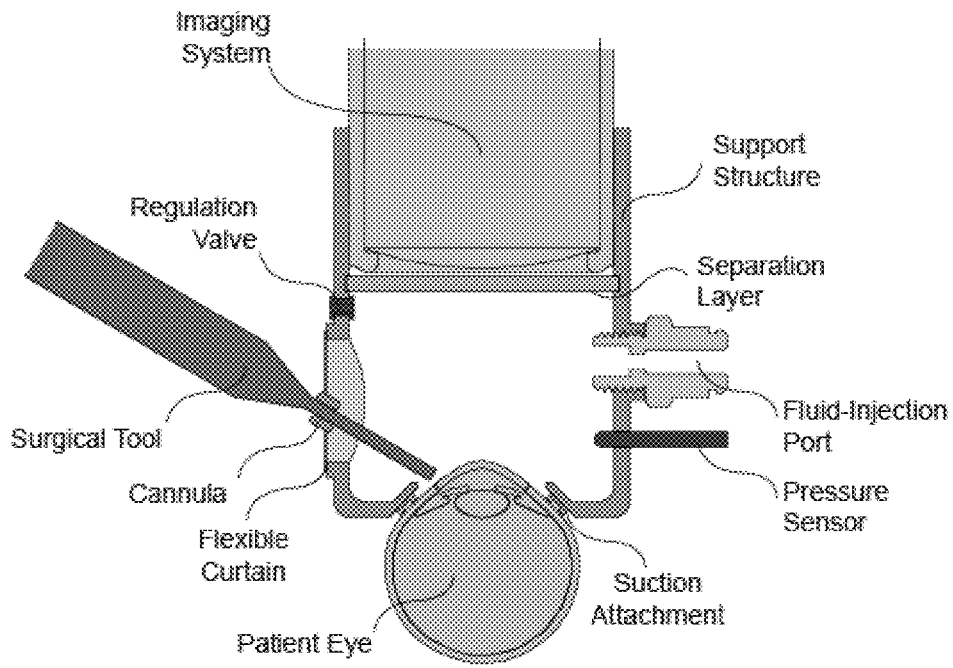
FIG. 10 shows the major difference in accommodating intraocular surgical tools with a prior art.
Figure 10:
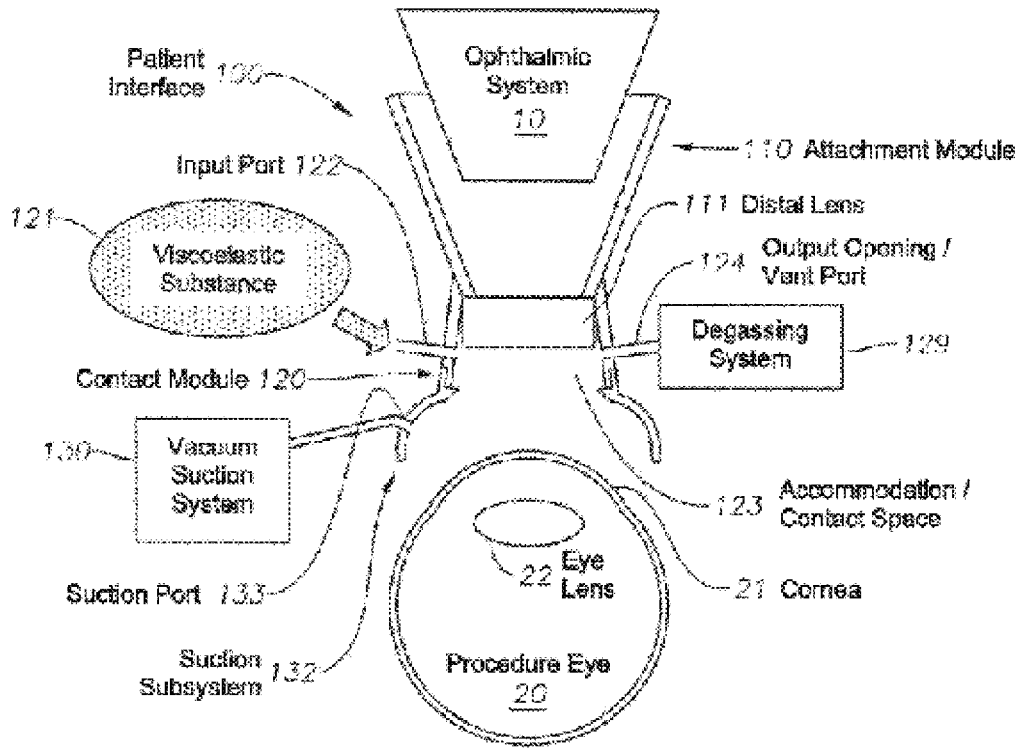

Referring to FIG. 10, the proposed device in the claim differs from pre-existing patient interface in that not only an unobstructed path is preserved for optical instruments while physically stabilizing the eyeball, but also intraocular surgical tools can be accommodated for maneuvers inside the eyeball.

Example Embodiments:

The following are example embodiments of this disclosure.

First Aspect

In some embodiments, a docking system for intraocular surgery includes: (1) a support structure having a first end to accommodate an imaging probe, and a second end to accommodate an eyeball, the support structure including a sidewall; (2) a separation layer disposed within an interior of the support structure to separate the interior into a sterile field and a non-sterile field; (3) a flexible port disposed extending through the sidewall of the support structure, to accommodate a surgical tool; and (4) a retaining mechanism disposed adjacent to the second end of the support structure, to secure the eyeball relative to the support structure.

In some embodiments, the separation layer is light transmissive.

In some embodiments, the flexible port includes a flexible curtain and a tool cannula extending through the flexible curtain.

In some embodiments, the retaining mechanism includes a suction attachment.

In some embodiments, the docking system further includes a fluid-injection port disposed extending through the sidewall of the support structure, to allow introduction of a fluid into the sterile field.

In some embodiments, the docking system further includes a pressure sensor to measure an internal pressure in the sterile field.

In some embodiments, the docking system further includes a regulation valve disposed extending through the sidewall of the support structure, to allow release of the fluid from the sterile field.

In some embodiments, the docking system further includes a barrier layer disposed within the interior of the support structure to separate the sterile field into a first region and a second region, and wherein the fluid-injection port is disposed extending through the sidewall of the support structure adjacent to the second region, to allow introduction of the fluid into the second region of the sterile field.

In some embodiments, the barrier layer is light transmissive.

Second Aspect

In additional embodiments, a docking system for intraocular surgery includes: (1) a support structure including a sidewall having a first end and a second end, and defining a hollow interior; (2) a separation layer disposed within the interior of the support structure to separate the interior into a sterile field adjacent to the second end, and a non-sterile field adjacent to the first end; (3) a tool port disposed extending through the sidewall of the support structure adjacent to the sterile field; (4) a fluid-injection port disposed extending through the sidewall of the support structure adjacent to the sterile field; (5) a regulation valve disposed extending through the sidewall of the support structure adjacent to the sterile field; and (6) a retaining mechanism disposed adjacent to the second end of the support structure.

In some embodiments, the separation layer is light transmissive.

In some embodiments, the tool port includes a flexible curtain and a tool cannula extending through the flexible curtain.

In some embodiments, the retaining mechanism includes a suction attachment.

In some embodiments, the docking system further includes a pressure sensor disposed extending through the sidewall of the support structure adjacent to the sterile field.

In some embodiments, the docking system further includes a barrier layer disposed within the interior of the support structure to separate the sterile field into a first region and a second region, and wherein the fluid-injection port and the regulation valve are disposed extending through the sidewall of the support structure adjacent to the second region.

In some embodiments, the barrier layer is light transmissive.

In some embodiments, the first region contains a gas.

As used herein, the singular terms "a," "an," and "the" may include plural referents unless the context clearly dictates otherwise. Thus, for example, reference to an object may include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the terms "connect," "connected," and "connection" refer to an operational coupling or linking.

Connected objects can be directly coupled to one another or can be indirectly coupled to one another, such as via one or more other objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a first numerical value can be "substantially" or "about" the same as a second numerical value if the first numerical value is within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

In the description of some embodiments, an object provided "on," "over," "on top of" or "below" another object can encompass cases where the former object is directly adjoining (e.g., in physical or direct contact with) the latter object, as well as cases where one or more intervening objects are located between the former object and the latter object.

Additionally, concentrations, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A docking system for intraocular surgery that is configured to simultaneously:
    (1) stabilize a position and an orientation of an eye during intraocular surgical procedures;
    (2) preserve an unobstructed path for optical instruments;
    (3) provide access to the eye that allows for tool movement;
    (4) maintain eyeball hydration and improve scan quality of an imaging system, the imaging system including an OCT system or a surgical microscope; and
    (5) maintain or control an intraocular pressure of the eye to a stable and specified level during surgical procedures.

2. The docking system of claim 1, comprising:
    a support structure having a first end to accommodate an imaging system, and a second end to accommodate an eyeball;
    a separation layer disposed within an interior of the support structure to separate the interior into a sterile field and a non-sterile field; and
    a retaining mechanism disposed adjacent to the second end of the support structure, to secure the eyeball relative to the support structure.

3. The docking system of claim 2, wherein the support structure further includes a side wall that fully covers the surgical fields for the intended ophthalmic surgical operations, and one or multiple flexible ports disposed extending through the side wall to accommodate surgical tools.

4. The docking system of claim 3, wherein the side wall separates a tool incision site from the imaging area with a configurable recess feature to preserve unobstructed optical path as well as one or multiple surgical tool entries.

5. The docking system of claim 3, further comprising a contact lens with cutouts that is configured to effectively increase the suction force.

6. The docking system of claim 2, wherein the separation layer is light transmissive.

7. The docking system of claim 2, wherein the tool access may include a flexible curtain and a tool cannula extending through the flexible curtain.

8. The docking system of claim 2, wherein the retaining mechanism includes a suction attachment.

9. The docking system of claim 2, further comprising a fluid-injection port disposed extending through the sidewall of the support structure, to allow introduction of a fluid into the sterile field.

10. The docking system of claim 9, further comprising one or more of:
    a pressure sensor to measure an internal pressure in the sterile field;
    a regulation valve disposed extending through the sidewall of the support structure, to allow release of the fluid from the sterile field; and
    a barrier layer disposed within the interior of the support structure to separate the sterile field into a first region and a second region, and wherein the fluid-injection port is disposed extending through the sidewall of the support structure adjacent to the second region, to allow introduction of the fluid into the second region of the sterile field, wherein the barrier layer is light transmissive.

11. The docking system of claim 1, comprising:
    a support structure including a sidewall having a first end and a second end, and defining a hollow interior;
    a separation layer disposed within the interior of the support structure to separate the interior into a sterile field adjacent to the second end, and a non-sterile field adjacent to the first end, wherein the separation layer is light transmissive;
    a tool port disposed extending through the sidewall of the support structure adjacent to the sterile field;

a fluid-injection port disposed extending through the sidewall of the support structure adjacent to the sterile field;

a regulation valve disposed extending through the sidewall of the support structure adjacent to the sterile field; and a retaining mechanism disposed adjacent to the second end of the support structure.

12. The docking system of claim 11, wherein the tool port includes a flexible curtain and a tool cannula extending through the flexible curtain.

13. The docking system of claim 11, wherein the retaining mechanism includes a suction attachment.

14. The docking system of claim 11, further comprising a pressure sensor disposed extending through the sidewall of the support structure adjacent to the sterile field.

15. The docking system of claim 11, further comprising a barrier layer disposed within the interior of the support structure to separate the sterile field into a first region and a second region, and wherein the fluid-injection port and the regulation valve are disposed extending through the sidewall of the support structure adjacent to the second region, wherein the barrier layer is light transmissive, and wherein the first region contains a gas.

* * * * *